(12) United States Patent
Reid et al.

(10) Patent No.: US 9,006,200 B2
(45) Date of Patent: Apr. 14, 2015

(54) MICRORNA-BASED APPROACH TO TREATING MALIGNANT PLEURAL MESOTHELIOMA

(71) Applicant: Asbestos Diseases Research Institute, Concord (AU)

(72) Inventors: Glen Reid, Balmain (AU); Nico van Zandwijk, Cabarita (AU)

(73) Assignee: Asbestos Diseases Research Foundation, Concord (AU)

( * ) Notice: Subject to any disclaimer, the term of this patent is extended or adjusted under 35 U.S.C. 154(b) by 0 days.

(21) Appl. No.: 13/801,010

(22) Filed: Mar. 13, 2013

(65) Prior Publication Data

US 2014/0275223 A1     Sep. 18, 2014

(51) Int. Cl.
| A61K 48/00 | (2006.01) |
|---|---|
| C07H 21/02 | (2006.01) |
| C07H 21/04 | (2006.01) |
| A61K 31/713 | (2006.01) |
| A61K 45/06 | (2006.01) |

(52) U.S. Cl.
CPC ............... *A61K 31/713* (2013.01); *A61K 45/06* (2013.01)

(58) Field of Classification Search
USPC .......................................... 536/24.5; 514/44
See application file for complete search history.

(56) References Cited

U.S. PATENT DOCUMENTS

| 8,524,681 B2 * | 9/2013 | Puri et al. .................... 514/44 A |
|---|---|---|
| 2009/0131356 A1 | 5/2009 | Bader et al. |
| 2011/0111041 A1 | 5/2011 | Brahmbhatt et al. |
| 2012/0177599 A1 | 7/2012 | Pass et al. |
| 2012/0259001 A1 | 10/2012 | Khvorova et al. |

FOREIGN PATENT DOCUMENTS

| WO | WO-2006/021894 A2 | 3/2006 |
|---|---|---|
| WO | WO-2009/027830 A2 | 3/2009 |

OTHER PUBLICATIONS

Wang et al. (BMB reports, 2009 vol. 42(11):725-730).*
Linsley et al. (Molecular and Cellular Biology, 2007 vol. 27:2240-2252).*
Brennecke, Julius et al., "Principles of MicroRNA-Target Recognition", PLoS Biology, Mar. 2005, vol. 3, Issue 3, e85.
Busacca, Sara et al.,"MicroRNA Signature of Malignant Mesothelioma with Potential Diagnostic and Pronostic Implications", Am J Respir Cell Mol Biol, vol. 42. pp. 312-319, 2010.
Finnerty, J.R. et al., "The miR-15/107 group of microRNA genes: evolutionary biology, cellular functions, and roles in human diseases", J Mol Biol. Sep. 24, 2010; 402(3): 491-509.
Kelly, Ronan J. et al., "Mesothelin targeted agents in clinical trials and in preclinical development", Mol Cancer Ther. Mar. 2012; 11(3):517-525.
Qi, Peng et al., "Virus-Encoded micro-RNAs: Future Therepeutic Targets?", Cellular & Molecular Immunology, vol. 3, No. 6, Dec. 2006, pp. 411-419.

(Continued)

*Primary Examiner* — Terra Cotta Gibbs
(74) *Attorney, Agent, or Firm* — Foley & Lardner LLP

(57) ABSTRACT

The invention relates to microRNA mimics, corresponding to the miR-15/107 family, and to methodology for using microRNA mimics to treat malignant pleural mesothelioma (MPM) by restoring regulation of the expression of target genes of the miR-15/107 family in MPM tumor cells.

7 Claims, 7 Drawing Sheets

(56) References Cited

OTHER PUBLICATIONS

Washimi, Kota etal., "Specific Epression of Human Intelectin-1 in Malignant Pleural Mesothelioma and Gastrointestinal Goblet Cells", PLoS ONE Jul. 2012, vol. 7, Issue 7, e39889.

Reid, Glen, "The microRNA miR-16 and its relatives are novel tumour suppressor genes in malignanat pleural mesothelioma", ALLC, Aug. 24, 2012, Asbestos Diseases Research Instittute University of Sydney.

Reid, Glen, "The microRNA miR-16 is a novel tumour suppressor gene in malignant pleural mesothelioma", iMig, Sep. 14, 2012, Asbestos Diseases Research Insitute University of Sydney.

Weber et al., "Identification of miRNA-103 in the cellular fraction of human peripheral blood as a potential biomarker for malignant mesothelioma—a pilot study," PLoS One, vol. 7, No. 1, e30221, 9 pages.

Balatti et al., "MicroTNAs dysregulation in human malignant pleural mesothelioma," *J. Thorac. Oncol.*, vol. 6, No. 5, pp. 844-851 (2011).

Reid et al., "Restoring expression of miR-16: A Novel approach to therapy for malignant pleural mesothelioma," *Annals of Oncology*, vol. 24, pp. 3128-3135 (2013).

* cited by examiner

SEQUENCE LISTING

<160> NUMBER OF SEQ ID NOS: 30

<210> SEQ ID NO 1
<211> LENGTH: 22
<212> TYPE: RNA
<213> ORGANISM: Homo sapiens

```
<400> SEQUENCE: 1
uagcagcaca uaauggutuug ug                                          22

<210> SEQ ID NO 2
<211> LENGTH: 22
<212> TYPE: RNA
<213> ORGANISM: Homo sapiens

<400> SEQUENCE: 2
uagcagcaca ucauggutua ca                                           22

<210> SEQ ID NO 3
<211> LENGTH: 22
<212> TYPE: RNA
<213> ORGANISM: Homo sapiens

<400> SEQUENCE: 3
uagcagcacg uaaauauugg cg                                           22

<210> SEQ ID NO 4
<211> LENGTH: 21
<212> TYPE: RNA
<213> ORGANISM: Homo sapiens

<400> SEQUENCE: 4
uagcagcaca gaaauauugg c                                            21

<210> SEQ ID NO 5
<211> LENGTH: 22
<212> TYPE: RNA
<213> ORGANISM: Homo sapiens

<400> SEQUENCE: 5
cagcagcaau ucauguuuug aa                                           22

<210> SEQ ID NO 6
<211> LENGTH: 21
<212> TYPE: RNA
<213> ORGANISM: Homo sapiens

<400> SEQUENCE: 6
cagcagcaca cugugguuug u                                            21

<210> SEQ ID NO 7
<211> LENGTH: 23
<212> TYPE: RNA
<213> ORGANISM: Homo sapiens

<400> SEQUENCE: 7
uagcagcggg aacaguucug cag                                          23

<210> SEQ ID NO 8
<211> LENGTH: 19
<212> TYPE: RNA
<213> ORGANISM: Homo sapiens

<400> SEQUENCE: 8
aagcagcugc cucugaggc                                               19

<210> SEQ ID NO 9
<211> LENGTH: 23
<212> TYPE: RNA
<213> ORGANISM: Homo sapiens
```

```
<400> SEQUENCE: 9
agcagcauug uacagggcua uga                                          23

<210> SEQ ID NO 10
<211> LENGTH: 23
<212> TYPE: RNA
<213> ORGANISM: Homo sapiens

<400> SEQUENCE: 10
agcagcauug uacagggcua uca                                          23

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uagcagcaca uaaugguuug cg                                           22

<210> SEQ ID NO 12
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uagcagcaca uaaugguuug cgga                                         24

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uagcagcaca uaaugguuug cu                                           22

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uagcagcaca guaugguuug cg                                           22

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cgcaaaccau uaugugcugc ua                                           22
```

<210> SEQ ID NO 16
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uccgcaaacc auuaugugcu gcua                                           24

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
agcaaaccau uaugugcugc ua                                             22

<210> SEQ ID NO 18
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
cgcaaaccau acugugcugc ua                                             22

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cgcaaaccau uaugugcugc uu                                             22

<210> SEQ ID NO 20
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uccgcaaacc auuaugugcu gcuu                                           24

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
agcaaaccau uaugugcugc uu                                             22

```
<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cgcaaaccau acugugcugc uu                                            22

<210> SEQ ID NO 23
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cgcaaaccau uaugugcugc uuua                                          24

<210> SEQ ID NO 24
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uccgcaaacc auuaugugcu gcuuua                                        26

<210> SEQ ID NO 25
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
agcaaaccau uaugugcugc uuua                                          24

<210> SEQ ID NO 26
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
cgcaaaccau acugugcugc uuua                                          24

<210> SEQ ID NO 27
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cgcaaaccau uaugugcugc uuua                                          24
```

-continued

```
<210> SEQ ID NO 28
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uccgcaaacc auuauugugc ugcuuua                                           27

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
agcaaaccau uauugugcug cuuua                                             25

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cgcaaaccau acuugugcug cuuua                                             25
```

MICRORNA-BASED APPROACH TO TREATING MALIGNANT PLEURAL MESOTHELIOMA

SEQUENCE LISTING

The present application contains a sequence listing, which has been submitted in ASCII format via EFS-Web and which is hereby incorporated by reference in its entirety. The ASCII copy, created on Jun. 20, 2013, is named 104481-0102_SL.txt and is 6,399 bytes in size.

BACKGROUND OF THE INVENTION

1. Technical Field

The invention relates generally to the field of molecular biology and cancer. More specifically, the invention relates to microRNA mimics corresponding to the miR-15/107 family and related methods of using microRNA mimics to treat malignant pleural mesothelioma (MPM) by restoring the regulation of expression of target genes of the miR-15/107 family in MPM tumor cells.

2. Background

Malignant pleural mesothelioma is an almost invariably fatal cancer for which few treatments are available. New therapies are urgently needed, and dysregulated microRNA expression provides a source of novel therapeutic targets.

MicroRNAs are transcribed by RNA polymerase II (pol II) or RNA polymerase III (pol III). See Qi et al. (2006) *Cellular & Molecular Immunology*, Vol. 3: 411-19. They arise from initial transcripts, termed primary microRNA transcripts (pri-microRNAs), which generally are several thousand bases long. Pri-microRNAs are processed in the nucleus by the RNase Drosha into about 70- to about 100-nucleotide hairpin-shaped precursors (pre-microRNAs). Following transport, to the cytoplasm, the hairpin pre-microRNA is further processed by Dicer to produce a double-stranded mature microRNA. The mature microRNA strand is then incorporated into the RNA-induced silencing complex (RISC), where it associates with its target mRNAs by base-pair complementarity. In the relatively rare cases in which a microRNA base pairs perfectly with an mRNA target, it promotes mRNA degradation. More commonly, microRNAs form imperfect heteroduplexes with target mRNAs, affecting either mRNA stability of inhibiting mRNA translation.

Multiple studies have profiled mRNA gene expression in MPM to identify potential targets, and more recently, microRNA expression profiles have been generated, initially for diagnostic purposes using samples derived from normal and tumor cell lines, MPM tumors and pooled normal pericardium, or MPM and lung cancer. They also have been generated for prognostic purposes, i.e., within MPM tumors of different classification. See, e.g., Busacca et al., *Am. J. Respir. Cell. Mol. Biol.* 42: 312-19 (2010). However, none have made an extensive comparison between MPM tumors and normal pleural tissue.

Further, while relatively easy to use in vitro, microRNA mimics typically suffer, in terms of in vivo efficacy, due to two problems: (1) poor activity (including low RISC incorporation and off-target effects) and (2) inefficient delivery (related to stability and specific/selective distribution to the site of action).

As mentioned, multiple studies have profiled gene expression in MPM. This has been with the aim of understanding the disease process as well as to identify potential targets. These studies have characterized a general upregulation of metabolic and cell cycle genes in MPM, with additional changes in apoptotic genes associated with an altered apoptotic response linked to resistance to chemotherapy. To date, these studies have yet to reveal the overarching mechanism of genetic control of the phenotypes common to MPM tumors. However, as microRNAs are considered global modulators of gene expression, downregulation of expression of microRNAs represent a potential explanation for the upregulation of families of genes (i.e., loss of microRNA expression causes target gene upregulation).

SUMMARY OF THE INVENTION

The invention is based in part on the identification of a family of microRNAs that are down-regulated in MPM tumor samples as compared with normal pleural tissue from unaffected individuals. In particular, the inventors discovered a marked down-regulation in expression of the miR-15/107 family of microRNAs in MPM tissue.

Accordingly, one aspect of the present invention relates to a double-stranded microRNA mimic that is useful for the treatment of MPM. Such a miRNA mimic of the invention comprises:

(1) a mature sequence corresponding to a miR-15/107 family member and that contains AGCAGC at positions 2-7 or 1-6 at the 5' end; and (2) a passenger strand, which can be inactivated by chemical modification. The mature sequence can comprise a sequence selected from the group consisting of SEQ ID NOS: 11-14. The passenger strand can comprise a sequence selected from the group consisting of SEQ ID NOS: 15-18.

In accordance with another aspect, the invention provides a method for treating MPM in a subject suffering from the disease. The method comprises administering an effective amount of a double-stranded miRNA mimic, as described above, where such administration mimics endogenous expression of the miR-15/107 family, thereby restoring regulation of the expression of target genes of the miR-15/107 family in the subject. The administration preferably is effected using an intact, bacterially derived minicell for delivery of the miRNA mimic. Pursuant to the inventive methodology, the step of administering microRNA mimic comprises simultaneous or serial co-administration of an adjunct anti-cancer therapy to the subject.

In another aspect of the invention, a method is provided for increasing sensitivity of a MPM cancer cell to the cytotoxic effects of an anti-cancer therapy. The method comprises administering to the cell at least one miRNA mimic as described above, such that the sensitivity of the MPM cancer cell is increased.

These and other aspects of this invention are further described below.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended figures. These figures form a part of the specification. They illustrate particular embodiments of the invention and, hence, are not limiting of it.

DETAILED DESCRIPTION OF THE INVENTION

As noted, a key aspect of the invention is the identification of a family of microRNAs that are down-regulated in MPM tumor samples as compared with normal pleural tissue from unaffected individuals. Thus, a marked down-regulation of the expression of the miR-15/107 family of microRNAs occurs in MPM tissue.

In exemplary embodiments, therefore, the present invention relates to the design, synthesis, construction, composition, characterization and use of therapeutic microRNAs corresponding to the miR-15/107 family for treating MPM. More specifically, the invention is directed to microRNA mimics that act to restore expression of the miR-15/107 family in MPM tumor cells by mimicking the activity of the endogenous members of the miR-15/107 family, thereby re-establishing control of MPM cell growth. The microRNA mimics can therefore be used in a replacement therapy approach to restore expression of the miR-15/107 family in MPM cells.

In further exemplary embodiments, the microRNA mimics are modified to improve stability, reduce off-target effects and increase activity. Additional embodiments relate to the use of a minicell to deliver the microRNA mimics. In another aspect of the invention, microRNA mimics operate to enhance the efficacy of other clinically used drugs for the treatment of MPM.

The miR-15/107 Family

The miR-15/107 family was identified previously and is characterized as a microRNA super family in which each member contains the sequence AGCAGC starting at either the first or second nucleotide from the 5' end of the mature microRNA strand. It is believed that the miR-15/107 family is involved with the regulation of numerous cell activities that represent intervention points for cancer therapy and for therapy of other diseases and disorders. See Finnerty et al. (2010) *J. Mol. Biol.*, Vol. 402: 491-509, the contents of which are incorporated here by reference in its entirety. For instance, the miR-15/107 family is believed to be involved in regulating gene expression relating to cell division, metabolism, stress response and angiogenesis in vertebrate species, as well as human cancers, cardiovascular disease and neurodegenerative diseases.

Figure 1:
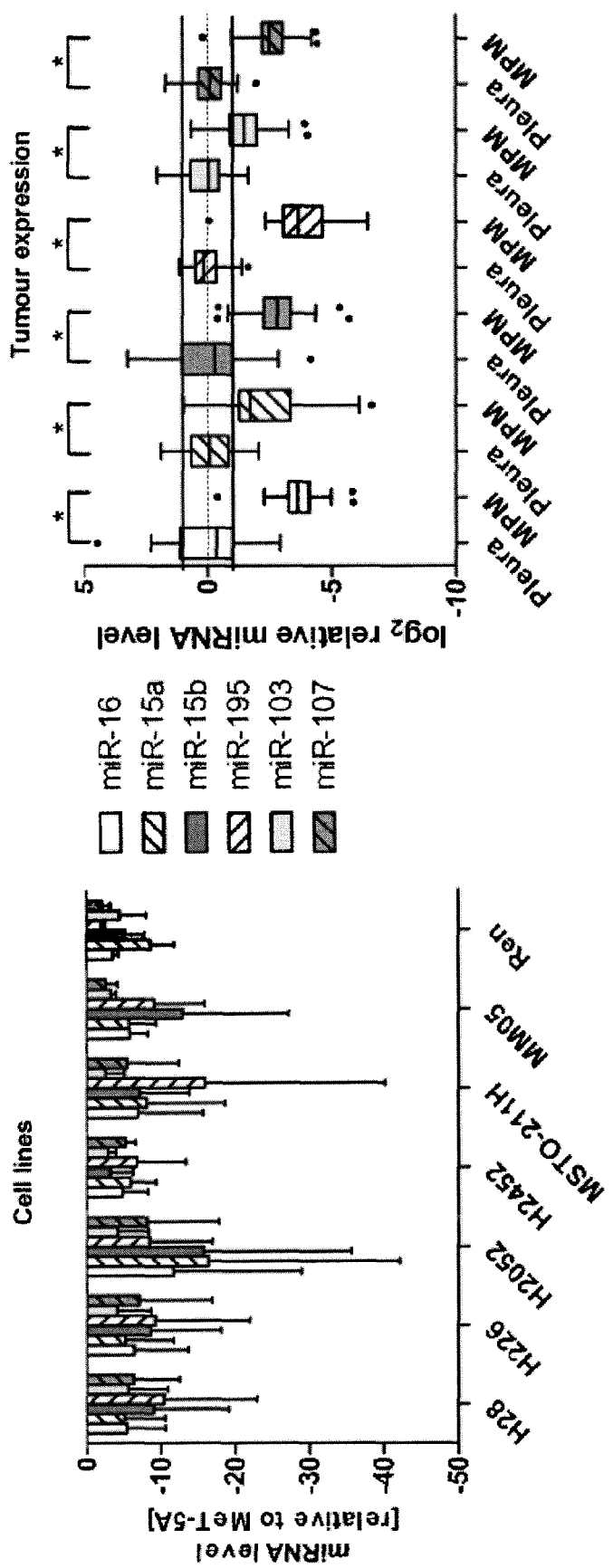
FIG. 1 depicts the expression of the miR-15/107 family which is downregulated in MPM cell lines and tumors.
Figure 2:
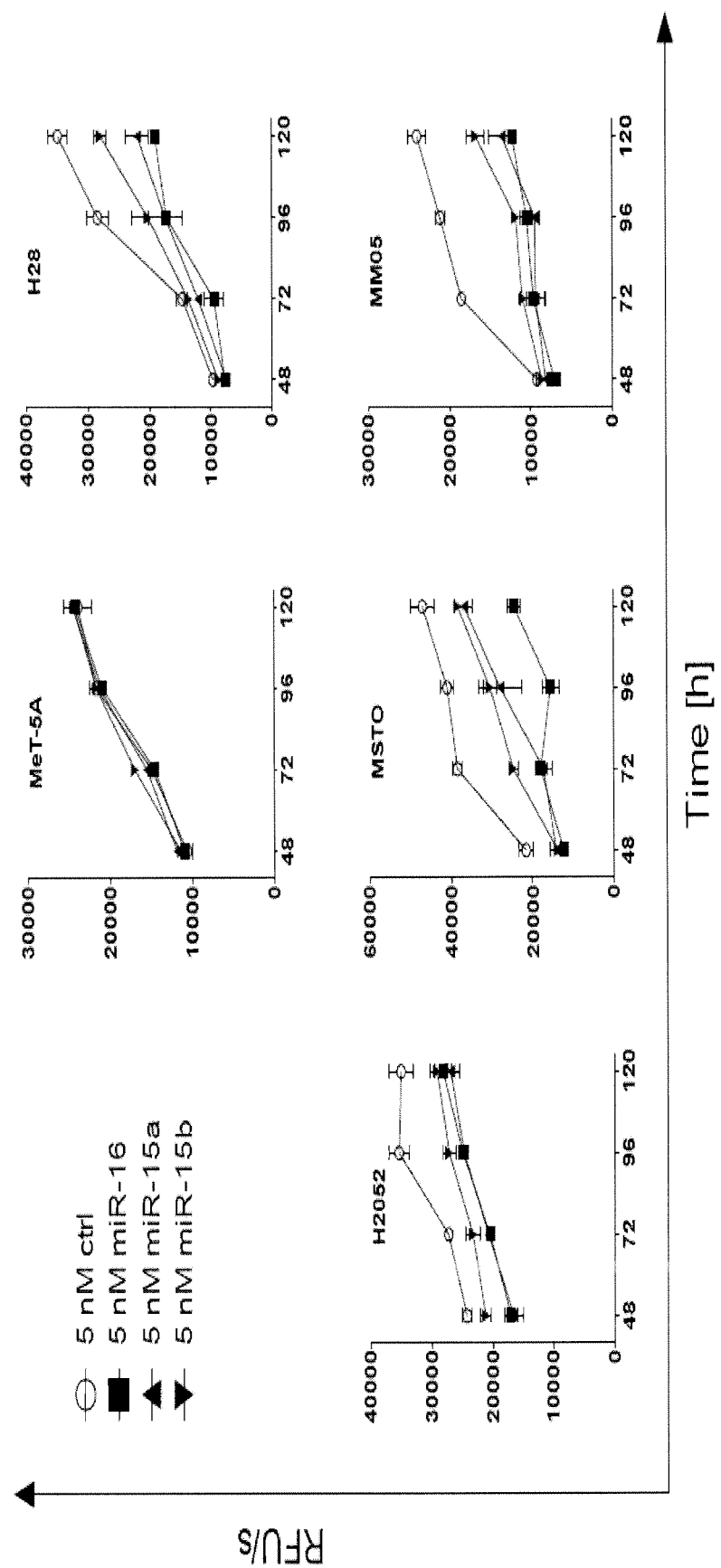
FIG. 2 illustrates that continuous chrysotile exposure reduces miR-15/107 family microRNA expression in MeT-5A immortalized mesothelial cells
Figure 3:
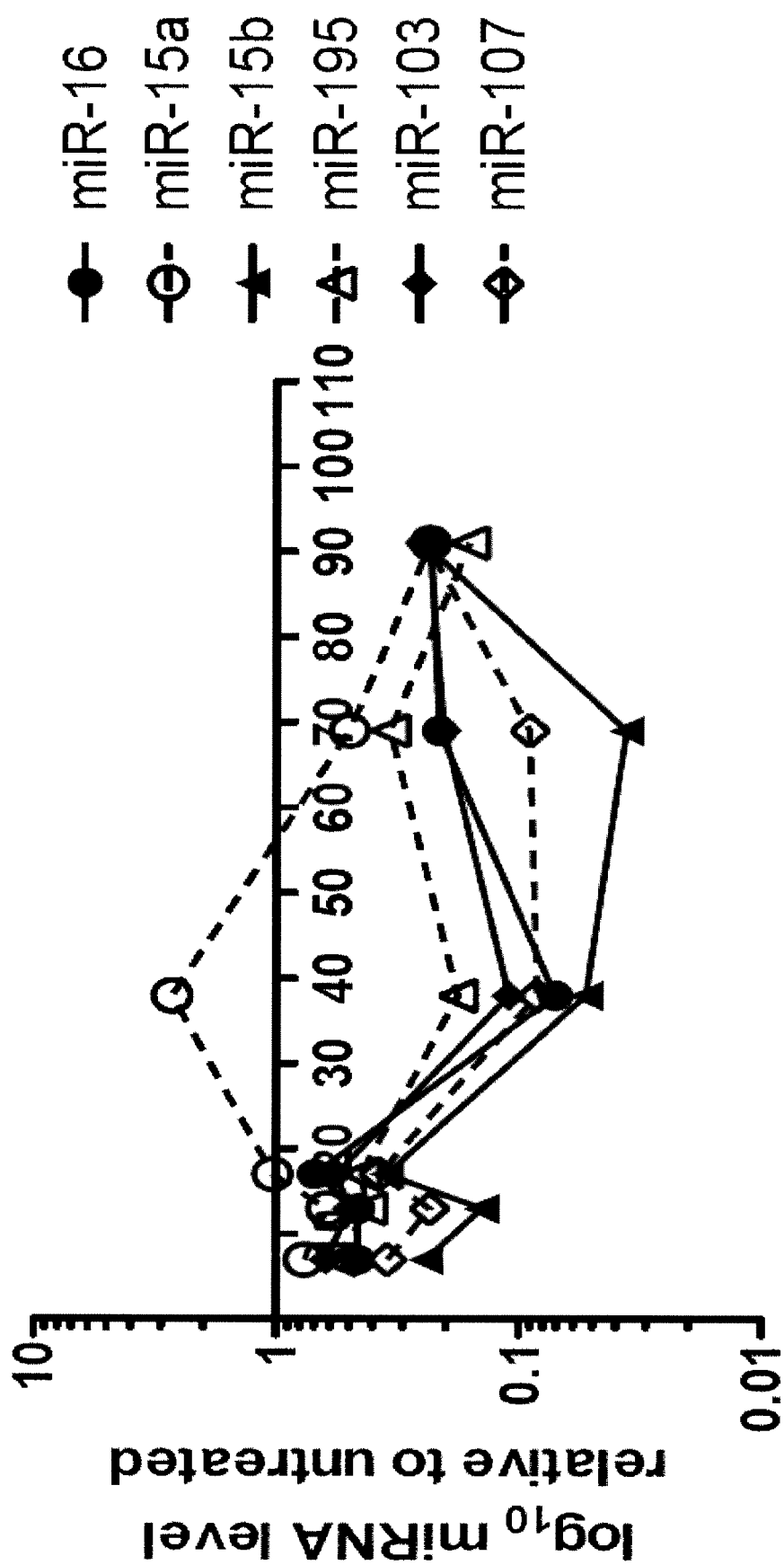
FIG. 3 depicts that replacing the miR-15/16 family leads to growth inhibition of MPM cells in vitro.
Figure 5:
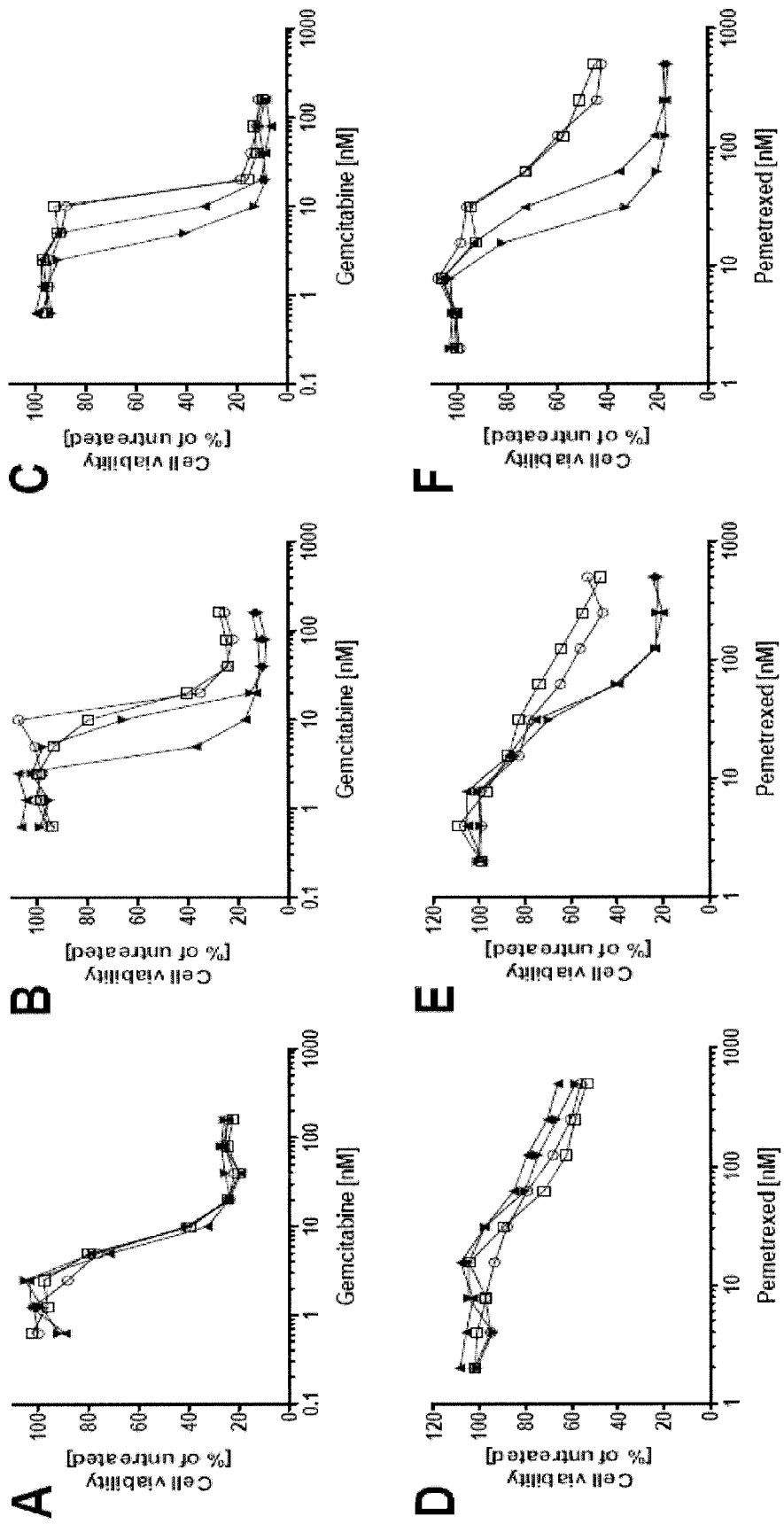
FIG. 5 illustrates that transfection with miR-16 downregulates target genes.
Figure 6:
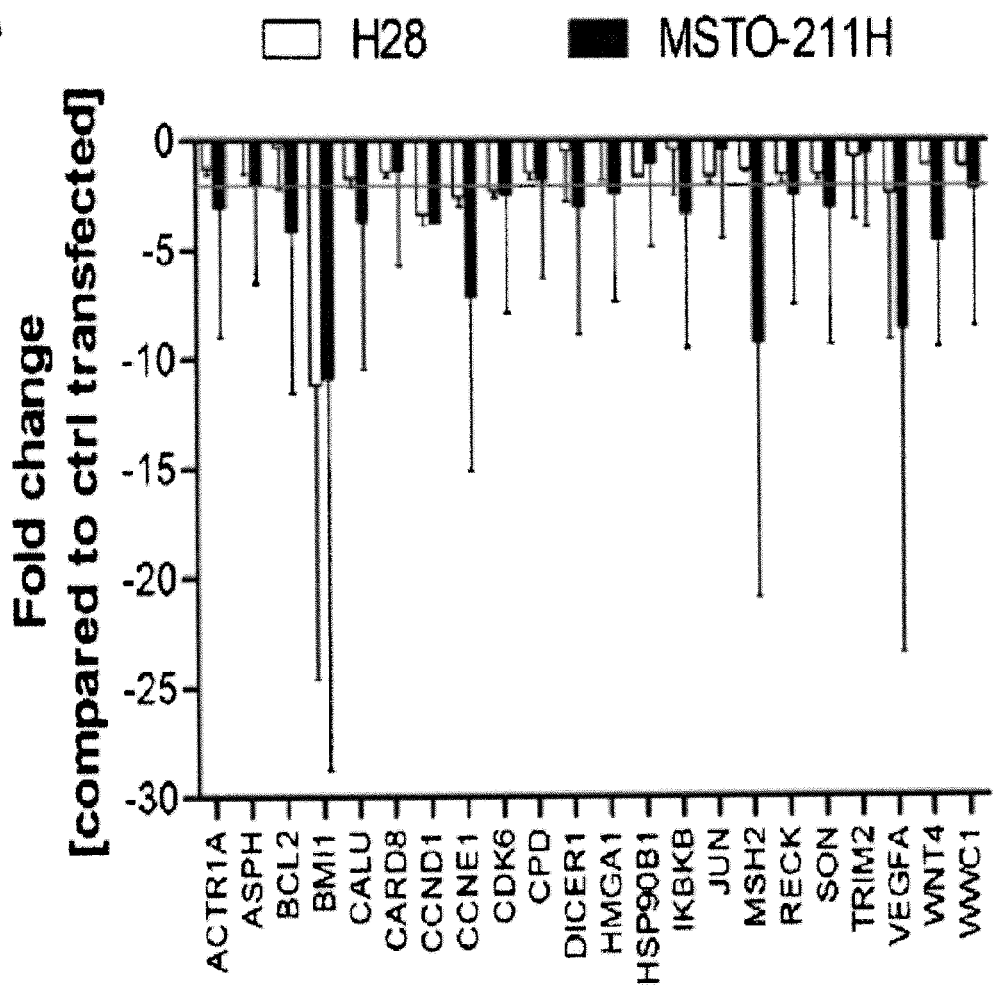
FIG. 6 depicts the effects of miR-16 on gemcitabine and pemetrexed toxicity in MPM cells.
Figure 6:
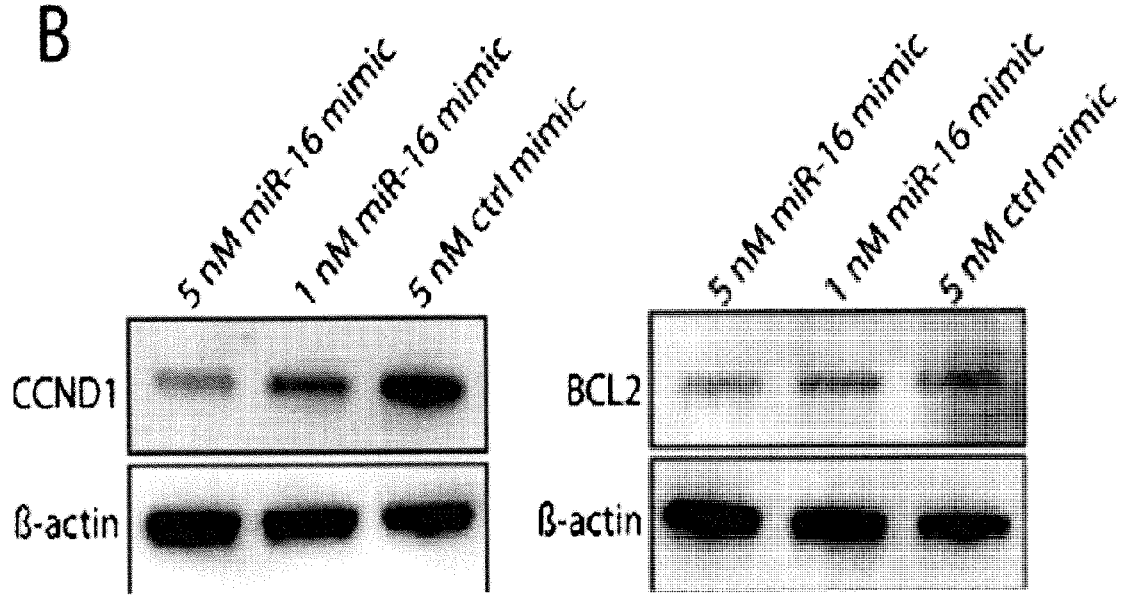

The search for novel approaches to developing cancer therapies often begins with attempts to identify differences between normal and tumor tissue to enable specific or selective targeting of tumor cells. For MPM this has proved difficult as many changes in gene expression, while specific to the tumor cells, are either unable to be targeted (i.e., non-druggable) or provide a therapeutic window that is too narrow (i.e., normal cells are affected). Furthermore, target expression is not always correlated with treatment success. While previous studies have indicated that a number of microRNAs have tumor-suppressor or oncogenic functions in MPM, these have not been observed to occur frequently in a large proportion of tumors or cell lines. In this context, the discovery that the entire miR-15/107 family is downregulated in all MPM cell lines and tumors analyzed (FIG. 1) provides a strong rationale for targeting these changes as a treatment approach. Together with data showing asbestos-induced downregulation of the miR-15/107 family of microRNAs (FIG. 2), this evidences an important causative role of these changes in MPM biology. In this regard, the identification of downregulation of the miR-15/107 family is significant for at least two reasons: first, it is highly specific for MPM (change is present in all samples, FIG. 1); second, it has no effect on normal mesothelial cells (FIG. 3). In addition, using a microRNA as a therapeutic entity for MPM provides the ability to correct, with a single agent, multiple aberrantly expressed genes (FIG. 5) responsible for increased proliferation and drug resistance (FIG. 6). To formulate microRNAs that are capable of restoring expression of the miR-15/107 family, the inventors considered characteristics such as sequence similarity in order to prepare an effective microRNA therapeutic approach.

The miR-15/107 family shares a common seed sequence, and thus the mRNA targets of each member overlap significantly. As used herein, the term "microRNA family" refers to a group of miRNA species that share identity across at least 6 consecutive nucleotides, also referred to as the "seed sequence," as described in Brennecke, J. et al., *PloS biol* 3 (3):pe85 (2005). As used herein, the term of "seed sequence" is used to denote nucleotides at positions 1-6, 1-7, 2-7, or 2-8 of a mature miRNA sequence. The microRNA seed sequence typically is located at the 5' end of the miRNA. As used herein, the term "mature sequence" refers to the strand of a fully processed microRNA that enters RISC.

Accordingly, for the purposes of the present invention the miR-15/107 family is comprised of ten sequences as follows:

```
miR 15a-5p
(SEQ ID NO: 1 uagcagcacauaaugguuugug, MI-
MAT0000068);

miR-15b-5p
(SEQ ID NO: 2 uagcagcacaucaugguuuaca, MI-
MAT0000417);

miR-16-5p
(SEQ ID NO: 3 uagcagcacguaaauauuggcg, MI-
MAT0000069);

miR-195-5p
(SEQ ID NO: 4 uagcagcacagaaauauuggc, MIMAT0000461);

miR-424-5p
(SEQ ID NO: 5 cagcagcaauucauguuuugaa, MI-
MAT0001341);

miR-497-5p
(SEQ ID NO: 6 cagcagcacacugugguuugu, MIMAT002820);

miR-503-5p
(SEQ ID NO: 7 uagcagcgggaacaguucugcag, MI-
MAT0002874);

miR-646-5p
(SEQ ID NO: 8 aagcagcugccucugaggc, MIMAT0003316);

miR-103a-3p
(SEQ ID NO: 9 agcagcauuguacagggcuauga, MI-
MAT0000101);
and miR-107
(SEQ ID NO: 10 agagcauuguacagggcuauca, MI-
MAT0000104).
```

To control all targets of the miR-15/107 family effectively, in theory all ten members would need to be reintroduced to MPM cells using microRNA mimics specific to each sequence listed above. Yet, this is not an efficient approach to clinical treatment. Instead, the invention provides a microRNA mimic approach in which a consensus sequence of the entire miR-15/107 family has been designed that operates as a mimic to perform the functions of the endogenous miR-15/107 family, thereby restoring expression of the miR-15/107 family in MPM cells (FIG. 3). As used in this description, the phrase "consensus sequence" refers to a nucleotide sequence that shares high sequence, structural and/or functional identity among a group of sequences. In this regard, a microRNA mimic comprising a consensus sequence is capable of mimicking the functions of the entire miR-15/107 family. The design of a consensus sequence of the entire miR-15/107 family therefore affords the advantage of maximizing the number of desired targets (i.e., the ten miR-15/107 family members) for which endogenous expression can be mimicked, while at the same time limiting the number of mimics to a single sequence entity.

Accordingly, in specific embodiments, the microRNA mimics are used as a form of replacement therapy to treat MPM cells, wherein the microRNA mimics are capable of performing the functions of the miR-15/107 family, thereby restoring expression of the miR-15/107 family. As such, in the context of this disclosure, the term "restoring expression" refers to the restoration of expression of the miR-15/107 family through the use of microRNA mimics that are capable of mimicking the functions of the endogenous miR-15/107 family.

microRNA Mimics

As used herein, the term "microRNA mimic" refers to synthetic non-coding RNAs that are capable of entering the RNAi pathway and regulating gene expression. As used herein, "synthetic microRNA" refers to any type of RNA sequence, other than endogenous microRNA. MicroRNA mimics imitate the function of endogeneous microRNAs and can be designed as mature, double-stranded molecules or mimic precursors (e.g., pri- or pre-microRNAs). MicroRNA mimics can be comprised of modified or unmodified RNA, DNA, RNA-DNA hybrids or alternative nucleic acid chemistries.

As disclosed above, the miR-15/107 family comprises ten microRNAs that share the sequence 5'-AGCAGC-3' at the 5'-terminal end of the active (guide) strand. The fact that all members of the miR-15/107 family have the same seed sequence provides an opportunity to correct global regulation of gene expression with a single microRNA mimic. Accordingly, the invention provides microRNA mimics corresponding to the miR-15/107 family which comprise a consensus sequence, wherein the microRNA mimics are capable of mimicking the endogenous activity of the entire miR-15/107 family. Therefore, restoration of microRNA expression is achieved through the use of these microRNA mimics.

Exemplary consensus sequences of the invention are as follows:

```
miR-15/107-consensus-1
(SEQ ID NO: 11 UAGCAGCACAUAAUGGUUUGCG);

miR-15/107-consensus-2
(SEQ ID NO: 12 UAGCAGCACAUAAUGGUUUGCGGA;

miR-15/107-consensus-3
(SEQ ID NO: 13 UAGCAGCACAUAAUGGUUUGCU);
``` and

```
miR 15/107-consensus-4
(SEQ ID NO: 14 UAGCAGCACAGUAUGGUUUGCG).

miR-15/107-complement-1
(SEQ ID NO: 15 CGCAAACCAUUAUGUGCUGCUA);

miR-15/107-complement-2
(SEQ ID NO: 16 UCCGCAAACCAUUAUGUGCUGCUA);

miR-15/107-complement-3
(SEQ ID NO: 17 AGCAAACCAUUAUGUGCUGCUA);

miR-15/107-complement-4
(SEQ ID NO: 18 CGCAAACCAUACUGUGCUGCUA);

miR-15/107-complement-1a
(SEQ ID NO: 19 CGCAAACCAUUAUGUGCUGCUU);

miR-15/107-complement-2a
(SEQ ID NO: 20 UCCGCAAACCAUUAUGUGCUGCUU);

miR-15/107-complement-3a
(SEQ ID NO: 21 AGCAAACCAUUAUGUGCUGCUU);

miR-15/107-complement-4a
(SEQ ID NO: 22 CGCAAACCAUACUGUGCUGCUU);

miR-15/107-complement-1b
(SEQ ID NO: 23 CGCAAACCAUUAUGUGCUGCUUUA);

miR-15/107-complement-2b
(SEQ ID NO: 24 UCCGCAAACCAUUAUGUGCUGCUUUA);

miR-15/107-complement-3b
(SEQ ID NO: 25 AGCAAACCAUUAUGUGCUGCUUUA);

miR-15/107-complement-4b
(SEQ ID NO: 26 CGCAAACCAUACUGUGCUGCUUUA);

miR-15/107-complement-1c
(SEQ ID NO: 27 CGCAAACCAUUAUGUGCUGCUUUA);

miR-15/107-complement-2c
(SEQ ID NO: 28 UCCGCAAACCAUUAUUGUGCUGCUUUA);

miR-15/107-complement-3c
(SEQ ID NO: 29 AGCAAACCAUUAUUGUGCUGCUUUA);
and miR-15/107-complement-4c
(SEQ ID NO: 30 CGCAAACCAUACUUGUGCUGCUUUA).
```

A preferred embodiment of the invention comprises a synthetic consensus microRNA ("guide") sequence in full or in part (SEQ IDs NO: 11-14), together with the complementary sequence as a passenger strand (SEQ IDs NO: 15-18). A double-stranded RNA mimic in which terminal mismatches and/or internal bulges are incorporated between the guide and passenger strand, which are introduced to increase RISC loading, is also contemplated by the invention (see SEQ ID NOs: 21-30). Other variations of the sequence corresponding to the consensus sequence of all family members, where the seed sequence AGCAGC is present within the first 7 nucleotides of the guide strand, i.e., positions 1-6 or positions 2-7, are also contemplated. Those skilled in the art will understand that other variations can promote RISC loading to increase activity. By way of example, these include a one or two nucleotide overhang at the 3' end of the guide strand; a DNA nucleotide (or other chemical modification) at the 3' end of the passenger strand.

Chemical Modifications

Generally, microRNA mimics have been found to be inefficient in operative use. In this regard, to improve efficiency the present invention employs a microRNA mimic comprising a structurally and chemically modified double-stranded RNA. In exemplary embodiments, in order to overcome the limitations of microRNA mimics, non-toxic chemical modifications to the mimic sequence have been introduced to improve stability, reduce off-target effects and increase activity.

In one embodiment, the microRNA mimic includes an RNA duplex comprising the mature microRNA sequence and a passenger strand. In one aspect, the passenger strand is structurally and chemically modified to enable the retention of activity of the duplex mimic while inactivating the passenger strand, thereby reducing off-target effects. In a further aspect, chemical modification inhibits nuclease activity, thereby increasing stability.

In particular embodiments, the microRNA mimics of the invention contemplate the use of nucleotides that are modified to enhance their activities. Such nucleotides include those that are at the 5' or 3' terminus of the RNA as well as those that are internal within the molecule. Modified nucleotides used in the complementary strands of microRNAs either block the 5'OH or phosphate of the RNA or introduce internal sugar modifications that prevent uptake and activity of the inactive strand of the microRNA. Modifications for the microRNA inhibitors include internal sugar modifications that enhance hybridization as well as stabilize the molecules in cells and terminal modifications that further stabilize the nucleic acids in cells. Further contemplated are modifications that can be detected by microscopy or other methods to identify cells that contain the microRNAs.

In other aspects, modifications may be made to the sequence of a microRNA or a pre-microRNA without disrupting microRNA activity. As used herein, the term "functional variant" of a microRNA sequence refers to an oligonucleotide sequence that varies from the natural microRNA sequence, but retains one or more functional characteristics of the microRNA (e.g. enhancement of cancer cell susceptibility to chemotherapeutic agents, cancer cell proliferation inhibition, induction of cancer cell apoptosis, specific microRNA target inhibition). In some embodiments, a functional variant of a microRNA sequence retains all of the functional characteristics of the microRNA. In certain embodiments, a functional variant of a microRNA has a nucleobase sequence that is a least about 60%, 65%, 70%, 75%, 80%, 85%, 90%, 91%, 92%, 93%, 94%, 95%, 96%, 97%, 98% or 99% identical to the microRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the microRNA or precursor thereof under stringent hybridization conditions. Accordingly, in certain embodiments the nucleobase sequence of a functional variant may be capable of hybridizing to one or more target sequences of the microRNA.

In some embodiments, the complementary strand is modified so that a chemical group other than a phosphate or hydroxyl is at its 5' terminus. The presence of the 5' modification apparently eliminates uptake of the complementary strand and subsequently favors uptake of the active strand by the microRNA protein complex. The 5' modification can be any of a variety of molecules known in the art, including $NH_2$, $NHCOCH_3$, and biotin.

In another embodiment, the uptake of the complementary strand by the microRNA pathway is reduced by incorporating nucleotides with sugar modifications in the first 2-6 nucleotides of the complementary strand. It should be noted that such sugar modifications can be combined with the 5' terminal modifications described above to further enhance microRNA activity. Sugar modifications contemplated in microRNA mimics include, but are not limited to, a sugar substitute group selected from: F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In some embodiments, these groups may be chosen from: $O(CH_2)_xOCH_3$, $O((CH_2)_xO)_yCH_3$, $O(CH_2)_xNH_2$, $O(CH_2)_xCH_3$, $O(CH_2)_xONH_2$ and $O(CH_2)_xON((CH_2)_xCH_3)_2$, where x and y are from 1 to 10.

Altered base moieties or altered sugar moieties also include other modifications consistent with the purpose of a microRNA mimic. Such oligomeric compounds are best described as being structurally distinguishable from, yet functionally interchangeable with, naturally occurring or synthetic unmodified oligonucleotides. As such, all such oligomeric compounds are contemplated to be encompassed by this invention so long as they function effectively to mimic the structure or function of a desired RNA oligonucleotide strand corresponding to the miR-15/107 family.

In some embodiments, the complementary strand is designed so that nucleotides in the 3' end of the complementary strand are not complementary to the active strand. This results in double-stranded hybrid RNAs that are stable at the 3' end of the active strand but relatively unstable at the 5' end of the active strand. This difference in stability enhances the uptake of the active strand by the microRNA pathway, while reducing uptake of the complementary strand, thereby enhancing microRNA activity.

Other modifications contemplated in the practice of the invention can be found in US Patent Pub. No. 2012/0259001, which is incorporated herein by reference in its entirety.

In some embodiments, microRNA sequences of the invention may be associated with a second RNA sequence that may be located on the same RNA molecule or on a separate RNA molecule as the microRNA sequence. In such cases, the microRNA sequence may be referred to as the active strand, while the encoded RNA sequence, which is at least partially complementary to the microRNA sequence, may be referred to as the complementary strand. The active and complementary strands may be hybridized to generate a double-stranded RNA that is similar to a naturally occurring microRNA precursor. The activity of a microRNA may be optimized by maximizing uptake of the active strand and minimizing uptake of the complementary strand by the microRNA protein complex that regulates gene translation. This can be done through modification and/or design of the complementary strand, for instance.

A nucleic acid may be made by any technique known to one of ordinary skill in the art, such as for example, chemical synthesis, enzymatic production or biological production. In some embodiments, microRNA compositions of the invention are chemically synthesized.

A preferred embodiment has a particular set of such modifications. These are chemical modification of 2 to 6 nucleotides at each end of the passenger strand with 2'O-methyl-modified sugars, and include any combination of 2, 3, 4, 5 or 6 modified nucleotides at the 5' end of the passenger strand with 2, 3, 4, 5 or 6 modified nucleotides at the 3' end of the passenger strand. Alternative chemical modification strategies imparting similar functionality will be apparent to those skilled in the art.

Method of Administration

MicroRNA mimics can be administered to a subject by any means suitable for delivering these compounds to cancer cells of the subject. For example, the microRNA mimics can be administered by methods suitable to transfect cells of the subject with the mimics, or with nucleic acids comprising sequences encoding these compounds. In one embodiment, the cells are transfected with a plasmid or viral vector comprising sequences encoding a microRNA mimic.

In one particular embodiment of the invention, to circumvent the problems associated with inefficient delivery in vivo, a mimic according to the invention preferably is delivered via the "EnGeneIC Delivery Vehicle" system developed by EnGeneIC Molecular Delivery Ltd. (Sydney), which is based on the use of intact, bacterially derived minicells. The EDV system is described, for example, in published international applications WO 2006/021894 and WO 2009/027830, the respective contents of which are incorporated here by reference.

In an exemplary embodiment, the microRNA mimics described here are delivered using intact, bacterially derived minicells or EnGeneIC delivery vehicles (EDVs). These EDVs are delivered specifically to target tissues using bispecific antibodies. One arm of such an antibody has specificity for the target tissue, while the other has specificity for the EDV. The antibody brings the EDVs to the target cell surface, and then the EDV is brought into the cell by endocytosis. After uptake into the tumor cell there is a release of the EDV contents, i.e., the microRNA mimic(s). For an antibody in this regard, specificity against any cell surface marker for MPM could be used in accordance with the invention. Thus, illustrative of such specificity suitable for a bispecific antibody in the present context could be a specificity to human mesothelin, expressed on 100% of epithelioid mesotheliomas, for which therapeutic antibodies are in development (see Kelly et al., *Mol. Cancer. Ther.* 11: 517-22 (2012)), or to intelectin-1, which is expressed specifically in MPM and gastrointestinal goblet cells (see Washimi et al., *PLoS One* 7: e39889 (2012)).

Other methods of administering nucleic acids are well known in the art. In particular, the routes of administration already in use for nucleic acid therapeutics, along with formulations in current use, provide preferred routes of administration and formulation for the nucleic acids. Nucleic acid compositions can be administered by a number of routes including, but not limited to: oral, intravenous, intrapleural, intraperitoneal, intramuscular, transdermal, subcutaneous, topical, sublingual, or rectal means.

Nucleic acids can also be administered via liposomes or nanoparticles. Such administration routes and appropriate formulations are generally known to those of skill in the art. Administration of the formulations described herein may be accomplished by any acceptable method that allows the microRNA or nucleic acid encoding the microRNA to reach its target. The particular mode selected will depend of course, upon exemplary factors such as the particular formulation, the severity of the state of the subject being treated, and the dosage required for therapeutic efficacy. As generally used herein, an "effective amount" of a nucleic acid is the amount that is able to treat one or more symptoms of cancer or related disease, reverse the progression of one or more symptoms of cancer or related disease, halt the progression of one or more symptoms of cancer or related disease, or prevent the occurrence of one or more symptoms of cancer or related disease in a subject to whom the formulation is administered, as compared to a matched subject not receiving the compound or therapeutic agent. The actual effective amounts of drug can vary according to the specific drug or combination thereof being utilized, the particular composition formulated, the mode of administration, and the age, weight, condition of the subject, and severity of the symptoms or condition being treated.

Other delivery systems suitable include but are not limited to time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these.

Pharmaceutical compositions of the invention containing microRNA mimics can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (e.g., DTPA or DTPA-bisamide) or calcium chelate complexes (e.g., calcium DTPA, CaNaDTPA-bisamide), or, optionally, additions of calcium or sodium salts (e.g., calcium chloride, calcium ascorbate, calcium gluconate or calcium lactate).

Dosing

As the relationship between loss of microRNA expression and MPM is consistent across the samples, one aspect of the invention is directed to microRNA replacement in MPM tumor cells. In this aspect, based on initial animal experiments, it is contemplated that the progression of MPM will be halted by treatment with the miR-containing miRs of the invention. In further aspects, it is contemplated that multiple doses over a continued time frame can be administered to the subject. In some aspects, although one dose per week may have a suitably efficacious effect, some subjects may demonstrate more markedly efficacious effects in response to increasing frequency and/or increasing dosage.

In another embodiment of the invention, chronic dosing will be able to achieve MPM disease control. In yet other embodiments, it is contemplated that MPM tumor cells receiving microRNA mimics will enter permanent growth arrest. In this regard, permanent growth arrest can be attributed to the mechanism of action of the microRNA mimics (downregulation of cell cycle- and metabolism-promoting genes, anti-apoptotic pro-survival genes, and drug resistance genes) and phenotypic consequences (cell cycle arrest). Continued treatment thus is contemplated, in accordance with one aspect of the invention, to induce disease control or maintenance (i.e., stable disease). Pursuant to aspect of the invention, tumor regression (i.e., a partial/complete response) is contemplated where the MPM tumors enter permanent cell growth arrest.

Furthermore, as discussed in further detail below, the microRNA mimics of the invention further function to sensitize cells to conventional cancer therapies such as chemotherapy and radiation. In this aspect, it is contemplated that combining the mimics with chemotherapy will provide additional therapeutic effects.

With all current treatments for MPM, response to therapy is invariably followed by relapse. Thus, in yet another aspect of the invention it is contemplated that tumors will retain this expression profile upon relapse in view of the relationship between microRNA expression and MPM. In this regard, a relapse as described will allow re-treatment with the same microRNA mimics disclosed herein. In this embodiment, long-term tumor suppression changes the nature of disease and potentially changes MPM into a form of chronic disease.

In other aspects, dosages for a particular subject can be determined by one of ordinary skill in the art using conventional considerations, (e.g., by means of an appropriate, conventional pharmacological protocol). A physician may, for example, prescribe a relatively low dose at first, subsequently increasing the dose until an appropriate response is obtained. The dose administered to a subject is sufficient to effect a beneficial therapeutic response in the subject over time, or, e.g., to reduce symptoms, or other appropriate activity, depending on the application. The dose is determined by the efficacy of the particular formulation, and the activity, stability or serum half-life of the microRNA employed and the condition of the subject, as well as the body weight or surface area of the subject to be treated. The size of the dose is also determined by the existence, nature, and extent of any adverse side-effects that accompany the administration of a particular vector, and formulation, in a particular subject.

Combination Therapy

The microRNA mimics described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the microRNA mimics can also be administered in therapeutically effective amounts as a portion of an anti-cancer cocktail. An anti-cancer cocktail is a mixture of the microRNA mimic(s) with one or more anti-cancer drugs in addition to a pharmaceutically acceptable carrier for delivery. The use of anti-cancer cocktails as a cancer treatment is routine.

In one embodiment, it is envisioned to use a microRNA mimic in combination with other therapeutic modalities. Thus, in addition to the microRNA therapies described above, one may also provide to the subject more "standard" therapies such as, but not limited to, conventional cancer therapeutic agents.

Anti-cancer drugs that are well known in the art and can be used as a treatment in combination with the nucleic acids described herein include, but are not limited to: actinomycin D, aminoglutethimide, asparaginase, bleomycin, busulfan, carboplatin, carmustine, chlorambucil, cisplatin (cis-DDP), cyclophosphamide, cytarabine HCl (cytosine arabinoside), dacarbazine, factinomycin, daunorubicin HCl, doxorubicin HCl, Estramustine phosphate sodium, etoposide (VP 16-213), floxuridine, 5-fluorouracil (5-FU), flutamide, hydroxyurea (hydroxycarbamide), Ifosfamide, Interferon apha-2a, interferon alpha-2b, leuprolide acetate (LHRH-releasing factor analog), lomustine, mechlorethamine HCl (nitrogen mustard), melphalan, mercaptopurine, mesna, methotrexate (MTX), mitomycin, mitoxantrone hcl, octreotide, plicamycin, procarbazine hcl, streptozocin, tamoxifen citrate, thioguanine, thiotepa, vinblastine sulfate, vincristine sulfate, amsacrine, azacitidine, hexamethylmelamine, interleukin-2, mitoguazone, pentostatin, semustine, teniposide, and vindesine sulfate.

Chemotherapeutic agents, for example, can be agents that directly cross-link DNA, agents that intercalate into DNA, and agents that lead to chromosomal and mitotic aberrations by affecting nucleic acid synthesis. Agents that directly cross-link nucleic acids, specifically DNA, are envisaged and are shown herein, to eventuate DNA damage leading to a synergistic antineoplastic combination. Agents such as cisplatin, and other DNA alkylating agents may be used. Agents that damage DNA also include compounds that interfere with DNA replication, mitosis, and chromosomal segregation. Examples of these compounds include adriamycin (also known as doxorubicin), VP-16, also known as etoposide, verapamil, podophyllotoxin, and the like. Exemplary chemotherapeutics include at least I) antibiotics, such as doxorubicin, daunorubicin, mitomycin, Actinomycin D; 2) platinum-based agents, such as cisplatin; 3) plant alkaloids, such as taxol and vincristine, vinblastine; 4) alkylating agents, such as carmustine, melphalan, cyclophosphamide, chlorambucil, busulfan, and lomustine.

In exemplary embodiments of the invention, the microRNA mimic(s) can be administered as a single agent but can also be used in combination with other drugs, e.g., pemetrexed, cisplatin (or carboplatin), and gemcitabine, etc.

Combination therapies may be achieved by contacting MPM tumor cells with a single composition or a pharmacological formulation that includes one or more microRNA mimics and a second cancer therapeutic agent, or by contacting the tumor cell with two distinct compositions or formulations, at the same time, wherein one composition includes one or more microRNA mimics and the other includes the second cancer therapeutic agent. Alternatively, administration of one or more microRNA mimics may precede or follow administration of the other cancer therapeutic agent by intervals ranging from minutes to weeks. In embodiments where the other cancer therapeutic agent and one or more microRNA mimics are applied separately to the subject, one would generally ensure that a significant period of time did not expire between the time of each delivery, such that the cancer therapeutic agent and the one or more microRNA mimics would still be able to exert an advantageously combined effect on the tumor cell.

Further pharmacological therapeutic agents and methods of administration, dosages, etc., are well known to those of skill in the art (see, for example, the "Physicians Desk Reference," Klaasen's "The Pharmacological Basis of Therapeutics," "Remington's Pharmaceutical Sciences," and "The Merck Index, Eleventh Edition," incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

EXAMPLES

The following examples are given for the purpose of illustrating various embodiments of the invention. They are not meant to limit the invention in any fashion. One skilled in the art will appreciate that the invention is well adapted to carry out the objects and obtain the ends and advantages mentioned, as well any objects, ends and advantages inherent herein. The present examples (along with the methods described herein) are presently representative of preferred embodiments. They are exemplary, and are not intended as limitations on the scope of the invention. Variations and other uses which are encompassed within the spirit of the invention as defined by the scope of the claims will occur to those skilled in the art.

Example 1

Discovery of the Reduced Expression of the miR-15/107 Family in MPM

MicroRNAs have important roles in cancer development and their expression is dysregulated in tumors, including MPM. The inventors identified changes in the miR-16 expression in MPM cell lines and a small set of tumor samples, and further assessed expression of the entire miR-15/107 family of related microRNAs in MPM cell lines and a larger set of tumor specimens.

A panel of 7 MPM cell lines was compared with a mesothelial cell line MeT-5A. Cells were obtained from ATCC(H28, H2052, H2452, H226 and MSTO-211H) and collaborators (MM05 and Ren) and cultured in the recommended medium at 37° C. with 5% $CO_2$. Total RNA was isolated from cells (grown to 80% confluence) using TriZOL® (Life Technologies). Sixty tumor specimens consisted of formalin-fixed, paraffin-embedded blocks. Tumor microRNA expression was compared with 23 formalin-fixed samples of normal pleural tissue. To isolate RNA from tumor specimens, an experienced pathologist marked tumor content on H&E stained slides from each block which were used as a guide for laser-capture microdissection to enrich tumor content. Briefly, samples were mounted onto membrane slides (Zeiss), and LCM was carried out using the PALM system (Zeiss). Captured tissue was collected in adhesive collection tubes, and deparaffinisation was performed in xylene. RNA was extracted from the captured tumor specimens and the normal tissues using the FFPE RNeasy Mini kit (Qiagen) according to the manufacturer's instructions. RNA from cell line and tissue samples was quantified using a Nanophotometer with readings at 260 and 280 nm. For both cell line and tumor samples, reverse transcription (RT) used microRNA-specific stem-loop primers (Life Technologies). 100 ng total RNA was used as template in the RT reaction, also including 4 µl RT primer mix (with up to 10 microRNA-specific RT primers multiplexed in an equimolar mix), with the reaction carried out following the manufacturer's instructions in a volume of 10 µl. The resultant complementary DNA (cDNA) was diluted by the addition of 57.8 µl water, and from this dilution, 2.25 µl cDNA was added as template to the qPCR reaction. The qPCR further contained microRNA-specific TaqMan primers/probes and TaqMan GeneExpression Mastermix (both Life Technologies) with a total reaction volume of 10 µl. The reactions were set up manually and run in duplicate on a Mx3000P real-time PCR machine (Stratagene) with 10 min enzyme activation at 95° C. followed by 40 cycles of 15 sec denaturing at 95° C. and 60 sec annealing/elongation at 60° C. Cq (quantification cycle) values were determined applying adaptive-baseline and background-based threshold algorithms using the MxPro software. Analysis of the qPCR results was performed using the $2^{-\Delta\Delta Cq}$ method (as described by Livak et al), and included normalization to RNU6B expression levels. Expression in each sample was calculated relative to the average expression of controls.

Of the ten microRNAs in the miR-15/107 family, 6 (miR-16, miR-15a, miR-15b, miR-195, miR-103 and miR-107) were detected in all samples, and 4 (miR-424, miR-497, miR-503 and miR-646) were undetected. In cell lines, an average 2- to 5-fold downregulation of all six detectable microRNAs was observed as compared to expression in immortalized normal mesothelial cells. In tumors, miR-16, miR-15a, miR-15b and miR-195 were downregulated by on average 8- to 25-fold, whereas miR-103 and miR-107 were downregulated by 4- to 6-fold, when compared with levels of these microRNAs in normal pleura.

Example 2

Reduction of miR-15/107 Family Expression Upon Exposure of MPM Cells to Chrysotile Asbestos Fibres Asbestos is the etiological agent in MPM, but effects on microRNA expression are unknown. Changes observed following asbestos exposure would suggest a causative role in MPM biology. Previous work in the field has focused on the effects on cells of acute exposure to cytotoxic concentrations of asbestos fibres. While changes in gene expression are observed in these cases, the predominant result of such treatment is a combination apoptosis and necrosis leading to extensive cytotoxicity and cell death.

In order to identify the physiologically relevant effects of asbestos exposure on microRNA expression in mesothelial cells, MeT-5A cells were continuously exposed to chrysotile asbestos fibres. MeT-5A cells were grown in recommended culture conditions in the presence of 0, 0.1 or 1 µg chrysotile asbestos fibres continuously for 3 months. At the indicated time points, cells were harvested and RNA isolated for microRNA expression measurements. RNA isolation and RT-qPCR was carried as described in Example 1. Levels of microRNA were normalized to U6 expression and are expressed relative to the normalized expression in untreated cells. FIG. 2 demonstrates that continuous exposure to asbestos at 1 µM leads to decreased expression of miR-16, miR-15b, miR-195, miR-103 and miR-107 at all time points, and decreases in miR-15a expression from 70 days on. These results are the first to link asbestos exposure to changes in microRNA expression in general, and the first to analyze changes in gene expression related to long-term asbestos exposure. They provide a direct link between asbestos exposure and miR-15/107 family expression, and thus suggest that these may be early and important changes in MPM progression.

Example 3

Replacing miR-15/107 Family Leads to Growth Inhibition of MPM Cells In Vitro

In order to determine the effects of restoring miR-15/107 family members on MPM cell growth, MPM cell lines were transfected with microRNA mimics and the effect on cell growth measured. Mimics consisted of double-stranded RNAs corresponding to the sequence of mature miR-16, miR-15a or miR-15, or a synthetic sequence corresponding to the consensus sequence of the miR-15/107 family, and were provided as HPLC-purified lyophilized duplexes (Shanghai GenePharma). Mimics were re-suspended in water at a concentration of 20 µM. These were then reverse transfected into cells using Lipofectamine RNAiMAX ('LRM', Life Technologies) at the indicated concentrations. First, lipoplexes were generated by mixing the appropriate concentration of mimic in serum-free medium with an equal volume of a 1% solution of LRM in serum-free medium, and incubating for 20 to 120 minutes at room temperature. Lipoplexes were distributed to replicate multiwell plates and cells in suspension (medium containing 10% FCS) were added to the lipoplex mix in each well such that the final density of cells was 7500/cm². Transfection was allowed to proceed for 24 hours after which medium was replaced with fresh medium containing 10% FCS and cells were further incubated at 37° C. until harvest. Thereafter, replicate plates were harvested at 48, 72, 96 and 120 hours post-transfection, which involved removing medium and freezing plates at −80° C. At the conclusion of the experiment, plates were thawed and 150 µl lysis buffer containing 0.01% SYBR Green added to each well to measure DNA content. After incubation overnight in the dark, DNA content was quantified by measuring fluorescence in a Fluostar Optima fluorimeter, set at excitation of 485 nm and emission 535 nm. Total fluorescence (i.e. DNA per well) in this assay displays a linear relationship with cell number, allowing it to determine proliferation.

Following transfection with microRNA mimics corresponding in sequence to miR-15a, miR-15b, or miR-16 there was a dose- and time-dependent decrease in proliferation in 4 MPM cell lines (H28, MM05, H2052 and MSTO). There was no effect of these treatments on the normal mesothelial cell line MeT-5A. Therefore, restoring microRNA expression and thus control of target gene expression resulted specifically in the inhibition of proliferation of MPM cells.

To investigate further the effects of the miR-15/107 family on MPM cells, mimics were designed that correspond to the consensus sequence of the family. The consensus mimics appear below.

TABLE 1

| Mimics | Sense (passenger) | Antisense (Guide) |
|---|---|---|
| con15/107.1 | mCmGmCmAAACCAUUAUGUGCUmGmCmUmA (SEQ ID NO: 15) | UAGCAGCACAUAAUGGUUUGCG (SEQ ID NO: 11) |
| con15/107.2 | mUmCmCmGCAAACCAUUAUGUGCUmGmCmUmA (SEQ ID NO: 16) | UAGCAGCACAUAAUGGUUUGCGGA (SEQ ID NO: 12) |
| con15/107.3 | mCmGmCmAAACCAUUAUGUGCUmGmCmUmA (SEQ ID NO: 17) | UAGCAGCACAUAAUGGUUUGCU (SEQ ID NO: 13) |
| con15/107.4 | mCmGmCmAAACCAUACUGUGCUmGmCmUmA (SEQ ID NO: 18) | UAGCAGCACAGUAUGGUUUGCG (SEQ ID NO: 14) |

Figure 4:
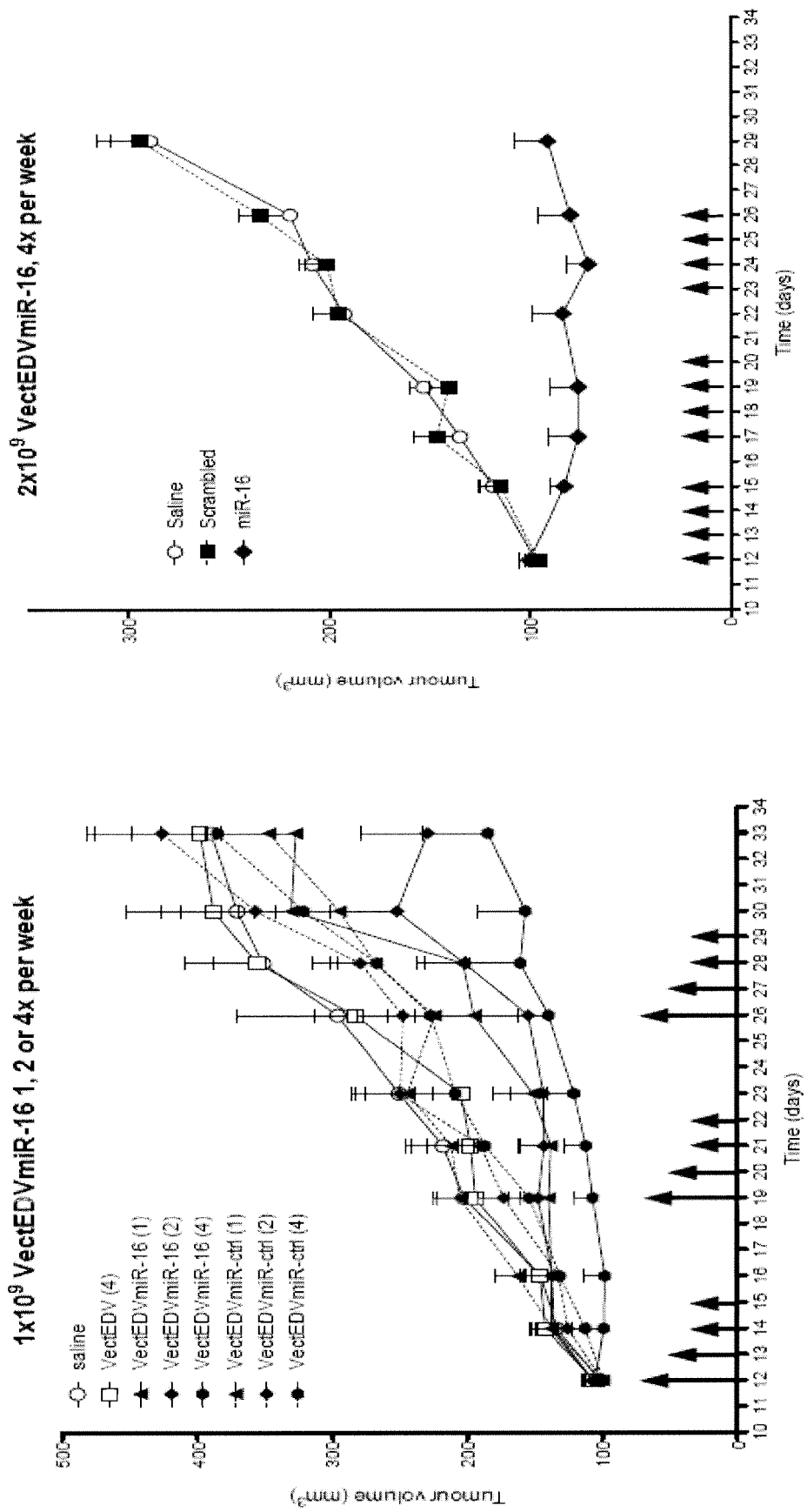
FIG. 4 shows that mimics comprising a sequence corresponding to the miR-15/107 consensus are more effective than native miR-16 in inhibiting MPM cell proliferation

These consensus sequences varied depending on the number of microRNAs included in the alignment, varying from the miR-15 family only (con15-107.1) to the entire 15/107 family (con15-107.2 to 4). The consensus length in con15-107.3 was increased to account for the longer mature sequence of some microRNAs. These 4 consensus microRNAs were then transfected into MSTO cells at varying concentrations and the effect on cell growth assessed as above. FIG. 4 shows that all 4 mimics based on the miR-15/107 consensus sequence were more growth inhibitory than the native miR-16 sequence. This suggests that the consensus sequences are more promising therapeutic candidates than the natural miR-16.

Example 4

Transfection with miR-16 Downregulates Target Genes

MicroRNAs are responsible for post-transcriptional gene regulation. While the primary mechanism of action of microRNAs is via inhibition of translation of mRNA into protein, this frequently leads to destabilization of target mRNA. Therefore, the ability of a microRNA to regulate gene expression of predicted targets can be measured by analyzing target mRNA levels following modulation of the microRNA of interest. Targets regulated in this way are then candidates for genes involved in the phenotypic effects observed following microRNA mimic transfection. Those genes also down-regulated at the protein level are considered more likely to be bona fide targets of the microRNA.

To link effects of mimic transfection on cell biology of MPM cells, expression of 24 candidate miR-16 target genes was measured in MPM cells treated with miR-16 mimic. H28 and MSTO cells were reverse transfected in 6-well plates, with miR-16 mimic or control (each 5 nM) as per the method described for Example 3. After 48 h transfection, RNA was isolated using TriZOL and quantified using a nanophotometer (Implen, Munich, Germany). From replicate wells, protein was isolated and quantified by Pierce BCA Protein assay (Thermo Fisher Scientific). Synthesis of cDNA used 250 ng RNA as template, with a mix of random oligos and oligodT as primers. This cDNA was then used as template in 10 µl qPCR reactions with primers specific for the predicted targets of miR-16, using Brilliant II SYBR green chemistry (Agilent Technologies) mix as per manufacturer's instructions, and the reactions were run on an MX3000P real time PCR machine (Agilent Technologies). The qPCR results were analyzed by the ΔΔCt method, whereby target gene expression was normalized to expression of 18S, and results from mimic-transfected cells expressed relative to the normalized expression of targets in control-transfected cells. These results demonstrated a down-regulation in 24 targets ranging from 1.2 to 4-fold. On the protein level, expression of CCND1 and Bcl-2 were analyzed by western blot. Protein (20 µg) was separated on a 10% precast polyacrylamide gel (Mini Protein TGX Precast Gels, Biorad) and transferred to PVDF membranes using the Biorad Trans-Blot Turbo Transfer System (Biorad, NSW, Australia). Membranes were blocked using milk powder then probed with target specific antibodies (Bcl-2; CCND1), followed by detection with a rabbit or mouse specific secondary antibody (all antibodies from Cell Signaling Inc). Chemiluminesence (Supersignal West Femto Maximum Sensitivity substrate kit, Thermo Fisher Scientific) was used to detect the presence of the protein and was measured using a Kodak Geologic 2200 imaging system. Expression of beta-actin (β-actin) was included to control for equal protein loading. Protein expression of both CCND1 and Bcl-2 were significantly down-regulated in miR-16 treated cells compared with controls. Together, these changes in mRNA and protein expression show that the observed phenotypic effects of miR-16 mimic transfection are related to genes involved in proliferation and altered apoptotic response.

Example 5

Effects of miR 16 on Gemcitabine and Pemetrexed Toxicity in MPM Cells

MPM is considered resistant to chemotherapy, and this resistance is believed to relate to changes in apoptotic responses of the tumor cells. As many of the predicted targets of the miR-15/107 family are genes related to these processes, one might predict that microRNA mimics would sensitize MPM cells to chemotherapy drugs. This was tested for the combination of miR-16 and the drugs gemcitabine and pemetrexed.

To test the effect of restoring miR-16 expression on drug toxicity, the normal mesothelial cell line MeT-5A (A, D), and two MPM lines—MM05 (B, E) and MSTO-211H (C, F)—were transfected with 1 or 5 nM miR-16 (closed symbols) or control mimic (closed symbols) in 96-well plates as described in Example 3. Thereafter, medium was replaced after 24 hours with medium containing a serial dilution of pemetrexed (1.95 to 500 nM) or gemcitabine (0.625 to 160 nM) with each concentration assayed in triplicate. After 72 hours, plates were harvested and DNA content measured as described in Example 3. The growth of cells exposed to drug was normalized to untreated cells, and the concentration inhibiting growth by 50% ($IC_{50}$ value) was determined. The effects of miR-16 on drug sensitivity was determined by comparing $IC_{50}$ values in mimic and control transfected cells. This demonstrated a dose-dependent 2- to 5-fold sensitization of MM05 (B, E) and MSTO-211H (C, F) cells to both drugs, but no effect on normal MeT-5A cells. (A, D).

Example 6

Effects of miR-16 Replacement in MPM In Vivo, Delivered as VectEDVmiR-16

The growth (and other) inhibitory effects observed upon restoration of lost expression of tumor suppressor microRNAs in cancer suggests that they represent novel therapeutic targets. In order to investigate this possibility, this must be tested in pre-clinical mouse models. In order to replicate these in vitro effects in the in vivo situation, however, the microRNA mimics must overcome hurdles limiting delivery to the cells within the tumor where they have their therapeutic effect. Here the delivery of miR-16 mimic was delivered using a targeted minicell approach. Minicells are nanoparticles derived from asynchronous division of bacteria, as disclosed above in reference to U.S. Patent Pub. No. 2011/0111041.

In vivo efficacy of miR-16 restoration was evaluated in a subcutaneous human xenograft model of MPM in nude mice. Athymic (nu/nu) mice (4-6 weeks old) were purchased from the Animal Resources Centre (Perth Western Australia) and all animal experiments were approved by the Sydney Local Health Districts Animal Ethics Committee, Concord and RPAH. MSTO cells were cultured and $1.5 \times 10^6$ cells in 50 µl serum-free media together with 50 µl growth factor reduced matrigel (BD Biosciences) and injected subcutaneously between the shoulder blades. Tumor volume ($mm^3$) was determined by measuring length (l) and width (w) and calculating volume ($V=lw^2/2$) as described on the indicated days. Experimental and control treatments were carried out once the tumor volumes were on average 100 $mm^3$, at which time the tumor mass was clearly palpable and vascularized, as determined following excision and histological examination of tumors. Mice were randomized to different groups before starting the various treatments. All tumor volume-measurements were performed by an investigator blinded to the treatments administered.

Two experiments were carried out. In the first experiment, mice were treated on the indicated days with indicated dose of $1 \times 10^9$ miR-16- or control-containing minicells 1, 2 or 4 times per week. The tumors in the control mice (treated with saline or empty minicells) increased from 100 to 400 $mm^3$ in the course of the experiment. Tumors in those mice receiving miR-16 mimic grew more slowly, and effects were dependent on number of treatments. Tumor-bearing mice receiving 1 dose per week had tumors that grew more slowly than those in control-treated mice, and this inhibition of growth was maintained until day 30, at which point the size of these tumors was similar to that of controls. Mice receiving 2 doses per week had tumors that increased in size to approximately 200 $mm^3$ by the end of the experiment on day 33, and were considerably smaller than those in mice receiving control minicells throughout. Mice treated 4 times per week had tumors that did not increase in size for the first week following the initial administration of the miR-16 mimic. By the end of the experiment, these tumors increased in size to only 170 mm3, corresponding to a 75% inhibition of growth when compared with controls.

In the second experiment, mice were treated 4 times per week with a dose of $2 \times 10^9$ miR-16 or control-loaded minicells. In this experiment, tumors in the mice treated with control minicells grew at a comparable rate to those in the first experiment that received half the dose. In mice receiving the increased dose of miR-16, there was a marked increase in anti-tumor effect of the miR-16 mimic. In the initial phase following treatment, the volume of these tumors decreased from the 100 $mm^3$ starting point. From there, tumor volume remained around 80 $mm^3$ and despite a slight increase following cessation of treatment on day 26 and the end of the experiment on day 29, remained below 100 $mm^3$. This corresponds to a complete inhibition of tumor growth in these miR-16-treated animals compared with saline and control-treated groups.

Figure 7:
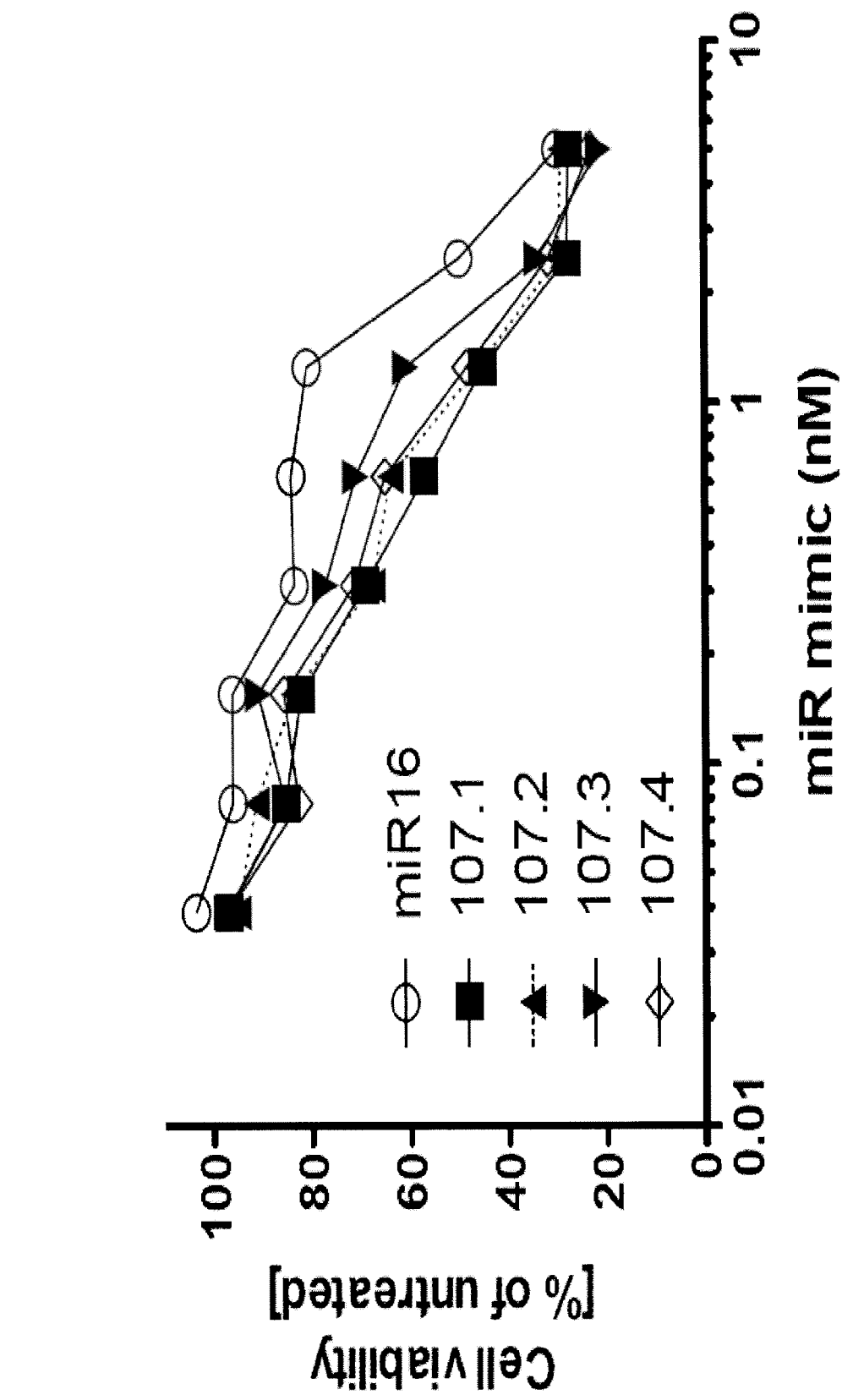
FIG. 7 depicts the effects of miR-16 replacement in MPM in vivo, delivered as $^{EGFR}$minicells$_{miR-16}$ (bispecific antibody targeted, miR-16-packaged minicells where the tumor cell targeting sequence in the bispecific antibody is directed to EGFR).

The inhibition of growth of MSTO-211H-derived xenograft tumors observed in mice following administration of $^{Vect}EDV_{miR-16}$ is exceptionally strong and exceeds the inhibition observed in vitro in cultures of the same (and other) MPM cells (compare FIG. 3 with FIG. 7). This is remarkable considering the fact that in vitro, >95% of cells are transfected with the miR mimic, whereas in vivo, the number of tumor cells receiving the mimic is likely to be ≤10%. It is likely that the observed effect is caused by the inhibitory effects of miR-16 (and other family members) on endothelial cells, thereby effectively targeting both tumor cells and stromal cells involved in angiogenesis that is required for tumor growth. It is noteworthy that the growth inhibitory effects of the mimic treatment in the subcutaneous xenograft model are greater than effects reported for other systemic treatments in the same model.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

The invention claimed is:

1. A double-stranded microRNA mimic for the treatment of malignant pleural mesothelioma (MPM), wherein the microRNA mimic comprises: (a) a consensus sequence of the miR-15/107 family, wherein the consensus sequence comprises a sequence selected from the group consisting of SEQ ID NOS: 11-14; and (b) a passenger strand.

2. A double-stranded microRNA mimic for the treatment of malignant pleural mesothelioma (MPM), wherein the microRNA mimic comprises: (a) a consensus sequence of the miR-15/107 family, wherein the consensus sequence contains AGCAGC at positions 2-7 at the 5' end but is different from the natural sequence of any miR-15/107 family member; and (b) a passenger strand, wherein the passenger strand comprises a sequence selected from the group consisting of SEQ ID NOS: 15-18.

3. The double-stranded microRNA mimic of claim 1 or 2, wherein the microRNA mimic comprises one or more nucleotides that are modified.

4. A double-stranded microRNA mimic for the treatment of malignant pleural mesothelioma (MPM), wherein the microRNA mimic comprises: (a) a consensus sequence of the miR-15/107 family, wherein the consensus sequence comprises a sequence that differs from any one of SEQ ID NOS: 11-14 by one or more nucleotides that are modified therefrom; and (b) a passenger strand.

5. The double-stranded microRNA mimic of claim 2, wherein the passenger strand is inactivated by chemical modification.

6. The double-stranded microRNA mimic of claim 1, wherein the passenger strand is inactivated by chemical modification.

7. The double-stranded microRNA mimic of claim 4, wherein the passenger strand is inactivated by chemical modification.

* * * * *